United States Patent
Yang (10) Patent No.: US 10,401,369 B2
(45) Date of Patent: Sep. 3, 2019

(54) METHOD FOR DISCRIMINATING PARKINSON'S DISEASE DEMENTIA FROM PARKINSON'S DISEASE WITH NORMAL COGNITION

(71) Applicant: MagQu Co. LTD., New Taipei (TW)

(72) Inventor: Shieh-Yueh Yang, New Taipei (TW)

(73) Assignee: MagQu Co. LTD., New Taipei (TW)

( * ) Notice: Subject to any disclaimer, the term of this patent is extended or adjusted under 35 U.S.C. 154(b) by 0 days.

(21) Appl. No.: 15/995,135

(22) Filed: Jun. 1, 2018

(65) Prior Publication Data
US 2018/0284138 A1    Oct. 4, 2018

Related U.S. Application Data

(63) Continuation-in-part of application No. 15/460,244, filed on Mar. 16, 2017, now abandoned.

(60) Provisional application No. 62/418,793, filed on Nov. 8, 2016.

(51) Int. Cl.
| | | |
|---|---|---|
| *H01F 1/34* | (2006.01) | |
| *G01N 33/50* | (2006.01) | |
| *G01N 33/68* | (2006.01) | |
| *G01N 33/543* | (2006.01) | |

(52) U.S. Cl.
CPC ..... *G01N 33/6896* (2013.01); *G01N 33/5005* (2013.01); *G01N 33/54326* (2013.01); *H01F 1/344* (2013.01); *G01N 2800/2835* (2013.01)

(58) Field of Classification Search
CPC ....... G01N 33/6896; G01N 2800/2835; G01N 33/5005; G01N 33/54326; H01F 1/344
See application file for complete search history.

(56) References Cited

U.S. PATENT DOCUMENTS

2008/0300204 A1*  12/2008  Federoff ............... C07K 16/18
514/44 R

OTHER PUBLICATIONS

Yang et al. Development of an ultra-high sensitive immunoassay with plasma biomarker for differentiating Parkinson disease dementia from Parkinson disease using antibody functionalized magnetic nanoparticles. J Nanobiotechnology. Jun. 8, 2016;14(1):41.*

* cited by examiner

*Primary Examiner* — Gregory S Emch
(74) *Attorney, Agent, or Firm* — Hannah Tien (57) ABSTRACT

The present invention provides a method for clinically identifying Parkinson disease with normal cognition or Parkinson disease dementia in a subject.

5 Claims, 5 Drawing Sheets

METHOD FOR DISCRIMINATING PARKINSON'S DISEASE DEMENTIA FROM PARKINSON'S DISEASE WITH NORMAL COGNITION

CROSS-REFERENCES TO RELATED APPLICATIONS

This application is a Continuation-in-Part application of the pending U.S. patent application Ser. No. 15/460,244 filed on Mar. 16, 2017 which claims priority to the provisional patent application No. 62/418,793 filed on Nov. 8, 2016, all of which are hereby incorporated by reference in their entirety. Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

BACKGROUND OF THE INVENTION

Field of the Invention

The present invention relates to method for clinically identifying Parkinson disease dementia from Parkinson disease.

Description of Prior Art

Parkinson disease (PD) is the second most common neurodegenerative disease after Alzheimer's disease. More than 1% of people older than 65 years old are suffering from PD. About 10 million people worldwide are living with PD. The direct and indirect healthcare cost for one PD patient is estimated to be US 100,000 per year. Many countries, especially the US, Canada, Europe and Australia, are worrying about unsustainable increases in the costs of healthcare. Lots of resources and effort have been put into developing the diagnosis, treatments and vaccine for PD.

The clinical criteria for diagnosing PD are the observations of movement disorders such as bradykinesia, cogwheel rigidity, resting tremor and postural instability. Although these clinical features are popularly used, there are several fatal issues for diagnosing PD. For example, other movement disorders (e.g. multiple system atrophy, corticobasal degeneration, or progressive supranuclear palsy) might overlap with the clinical symptoms of PD and decrease the accuracy of diagnosing PD. In addition, it has been reported the clinical symptoms are present after degeneration of over 50% of dopaminergic neurons in the basal ganglia, particularly in the substantia nigra. The early-stage diagnosis of PD is very difficult, using observations of clinical movement disorders. Analysis of the genetic sequence seems a better method for early-stage diagnosis of PD. Nevertheless, only 10% of PD patients are hereditary. Ninety percent of PD patients are sporadic.

Development of cognitive impairment and dementia, referred as Parkinson disease dementia (PDD), is common in PD. The prediction of development of dementia in PD is challenging and of significant impact in the field. Researchers are now trying to achieve bio-molecular diagnosis for differentiating PD from PDD. α-synuclein is the most recognized biomarker for PD or PDD. As α-synuclein molecules are phosphorylated, phosphor-α-synuclein molecules easily aggregate with one another to form Lewy body in the dopaminergic neurons. Dopaminergic neurons with Lewy bodies become degenerative and lose the ability to express dopamine Neural cells in the motor cortex of the brain are damaged due to the lack of dopamine and movement disorders are stimulated.

Numerous discoveries show the concentration of α-synuclein in the cerebrospinal fluid (CSF) is reduced because of the formation of Lewy bodies for PD or PDD patients as compared to healthy subjects. However, the reported results for the variations in the concentration of α-synuclein in blood are not consistent. The main reason for the inconsistent assay results for plasma α-synuclein is the poor low-detection limit of assays. According to these reports, the enzyme-linked immunosorbent assay (ELISA) is currently used for assaying α-synuclein in either CSF or plasma. α-synuclein is expressed and is abundant in the brain and spinal cord, but occurs in very low amounts in the peripheral blood system. ELISA is not able to precisely detect the proteins at ultra-low concentrations, such as α-synuclein in plasma. Thus, CSF instead of plasma is better for the assay of α-synuclein in the bio-molecular diagnosis of PD or PDD using ELISA.

CSF is usually collected via lumbar puncher, which is high-risk and uncomfortable. The early-stage diagnosis by assaying α-synuclein in CSF is not widely accepted by the general population. Alternatively, blood is much easier to obtain in clinics. Thus, a high-sensitivity detection technology is required to achieve the assay of ultra-low α-synuclein in plasma.

SUMMARY OF THE INVENTION

The present application provides a method for clinically identifying Parkinson disease with normal cognition or Parkinson disease dementia in a subject, comprising: (a) detecting in vitro immunomagnetic reduction (IMR) signals of α-synuclein in a blood sample of the subject, wherein the IMR signals are produced by binding α-synuclein with magnetic nanoparticles containing antibody against α-synuclein; (b) fitting the IMR signals of α-synuclein detected in step (a) to a logistic function (I) to calculate α-synuclein's concentration in the blood sample:

$$IMR(\%) = \frac{A-B}{1+\left(\frac{\varphi_{\alpha-syn}}{\varphi_o}\right)^\gamma} + B,$$

wherein IMR (%) is the IMR signals of α-synuclein, $\varphi_{\alpha-syn}$ is the concentration of α-synuclein, fitting parameter A is a background value, B is a maximum value, $\varphi_o$ is the concentration of α-synuclein when IMR signal equals ((A+B)/2), γ is a slope at data point $\varphi_o$ of a curve where $\varphi_{\alpha-syn}$ is x-axis and IMR (%) is y-axis; (c) comparing α-synuclein's concentration obtained in step (b) to two cut-off values, wherein α-synuclein's concentration higher than one cut-off value of 0.1 pg/ml is indicative of Parkinson disease with normal cognition, and α-synuclein's concentration higher than the other cut-off value of 1 pg/ml is indicative of Parkinson disease dementia; and (d) evaluating a treatment of the subject by consulting the α-synuclein's concentration.

DETAILED DESCRIPTION OF THE INVENTION

The inventors have developed an immunoassay technology, so-called immunomagnetic reduction (IMR), for quantitatively detecting bio-molecules at ultra-low concentrations, e.g. 1-10 pg/ml or lower. The main reason contributed to the ultra-high sensitivity of IMR is the utilization of antibody-functionalized magnetic nanoparticles. These magnetic nanoparticles are well dispersed in reagent and can catch target bio-molecules everywhere in a tested sample. Besides, due to the nano-scaled sizes of particles, the total binding area is extremely large. Hence, antibodies immobilized on the surfaces of magnetic nanoparticles are highly efficiently able to associate with target bio-molecules and result in an ultra-high sensitive immunoassay using IMR. It has been demonstrated IMR can be applied to assay ultra-low concentration β-amyloids and tau protein in human plasma. A clear discrimination between healthy subjects and patients with mild cognition impairment due to Alzheimer's disease was evidenced by assaying plasma β-amyloids and tau protein. These results motivated us to investigate the feasibility of assaying ultra-low concentration α-synuclein in human plasma to achieve a bio-molecular diagnosis of PD or PDD, or to differentiate PD from PDD according to the plasma α-synuclein concentration. In this work, the reagent for assaying α-synuclein by utilizing IMR is prepared. The characterizations of the reagent and assaying α-synuclein are explored. For comparison, the assay characteristics for α-synuclein using ELISA are examined. Finally, the preliminary results for discriminating PD patients, PDD patients and healthy subjects by assaying plasma α-synuclein are reported. Although the cross sectional study done in this work cannot address the prediction of the development of PDD in PD, the results might point to the potential use of this method of measuring plasma α-synuclein in differentiating PD from PDD.

The present application provides a method for clinically identifying Parkinson disease with normal cognition or Parkinson disease dementia in a subject, comprising: (a) detecting in vitro immunomagnetic reduction (IMR) signals of α-synuclein in a blood sample of the subject, wherein the IMR signals are produced by binding α-synuclein with magnetic nanoparticles containing antibody against α-synuclein; (b) fitting the IMR signals of α-synuclein detected in step (a) to a logistic function (I) to calculate α-synuclein's concentration in the blood sample:

$$IMR(\%) = \frac{A - B}{1 + \left(\frac{\varphi_{\alpha\text{-}syn}}{\varphi_o}\right)^\gamma} + B, \quad (I)$$

wherein IMR (%) is the IMR signals of α-synuclein, $\varphi_{\alpha\text{-}syn}$ is the concentration of α-synuclein, fitting parameter A is a background value, B is a maximum value, $\varphi_o$ is the concentration of α-synuclein when IMR signal equals ((A+B)/2), γ is a slope at data point $\varphi_o$ of a curve where $\varphi_{\alpha\text{-}syn}$ is x-axis and IMR (%) is y-axis; (c) comparing α-synuclein's concentration obtained in step (b) to two cut-off values, wherein α-synuclein's concentration higher than one cut-off value of 0.1 pg/ml is indicative of Parkinson disease with normal cognition, and α-synuclein's concentration higher than the other cut-off value of 1 pg/ml is indicative of Parkinson disease dementia; and (d) evaluating a treatment of the subject by consulting the α-synuclein's concentration.

In a preferred embodiment, material of the magnetic nanoparticles is selected from the group consisting of $Fe_3O_4$, $Fe_2O_3$, $MnFe_2O_4$, $CoFe_2O_4$ and $NiFe_2O_4$.

In another preferred embodiment, material of the magnetic nanoparticles is selected from the group consisting of $Fe_3O_4$.

In a further preferred embodiment, the blood sample is plasma.

In a further preferred embodiment, the IMR signals of α-synuclein in the blood sample of the subject is detected by using a machine capable of detecting IMR signals. In one preferred embodiment, the machine comprises a magnetic sensor capable of detecting IMR signals. In a more preferred embodiment, the machine comprises a magnetic sensor for detecting the IMR signals by immobilizing antibodies against α-synuclein onto magnetic nanoparticles. In one yet more preferred embodiment, the magnetic sensor comprises a superconducting quantum interference device (SQUID) or a IMRhigh-$T_c$ SQUID magnetometer for detecting the IMR signals.

In further preferred embodiment, the present invention further comprises a step, after step (d), of administering an effective amount of drug for treating Parkinson disease with normal cognition or Parkinson disease dementia to the subject whose α-synuclein's concentration is detected higher than the cut-off value of 0.1 pg/ml.

Examples

The examples below are non-limiting and are merely representative of various aspects and features of the present invention.

Method

The reagent for assaying α-synuclein consists of magnetic $Fe_3O_4$ nanoparticles (MF-DEX-0060, MagQu) functionalized monoclonal antibodies (sc-12767, Santa Crusz Biotech.) against α-synuclein. The detailed processes for immobilizing antibodies onto magnetic $Fe_3O_4$ nanoparticles are described in Horng et al. (IEEE Trans Appl Supercond. 2005; 15: 668-671) and Yang et al. (J Magn Magn Mater. 2008; 320: 2688-2691). The antibody-functionalized magnetic $Fe_3O_4$ nanoparticles are dispersed in pH-7.2 phosphate-buffered saline (PBS) solution. The distribution of particle diameters is analyzed by dynamic laser scattering (Nanotrac-150, Microtrac). The magnetic concentration of reagent is measured using a vibrating sample magnetometer (HysterMag, MagQu). The bio-activity of the antibodies on the magnetic nanoparticles is examined by an IMR analyzer (XacPro-S, MagQu). The IMR analyzer is an ac magnetosusceptometer equipped with a high-$T_c$ superconducting-quantum-interference-device (SQUID) magnetometer as a magnetic sensor. The details of the ac magnetosusceptometer are described in Yang et al. (IEEE Trans Appl Supercond. 2013; 23: 1600604-1600607) and Chieh et al. (J Appl Phys 2008, 103: 014703-1-6). To establish the relationship between the IMR signal and the concentration of α-synuclein, α-synuclein (ab51189, Abcam) spiked in PBS solutions is prepared. For each measurement of the IMR signal, 80-μl reagent is mixed with 40-μl α-synuclein solution, followed by detection of the IMR signal using an IMR analyzer (XacPro-S, MagQu). Duplicate measurements are performed for IMR signals with each concentration of α-synuclein solution. In addition to the measurements of the IMR signals, a commercial ELISA kit (KHB0061, Novex) is applied to find the α-synuclein concentration dependent optical absorbance unit.

Volunteers participating in this invention were given a medical checklist of major systemic diseases, operations and hospitalizations. Volunteers reporting uncontrolled medical conditions including heart failure, recent myocardial infarction (in the past 6 months), malignancy (in the past 2 years), or poorly controlled diabetes (HbAlC>8.5) were excluded. Volunteers also received physical examinations. The invention was approved by the ethics committee and institute review board of the university hospital.

Participants were asked to provide a 10-ml non-fasting venous blood sample (K3 EDTA, lavender-top tube). Each sample was assigned a registry number following the sampling sequence; hence, colleagues in the laboratory were blind to the clinical status and the demographic data of the subjects. The blood samples were centrifuged (2500 g for 15 min) within 1 h of collection and the plasma was aliquoted into cryotubes and stored at −80° C. for less than three months until being thawed for measurement via IMR. 80-μl of reagent was mixed with 40-μl of plasma for the measurement of α-synuclein concentration via IMR. Duplicate measurements were performed for each plasma sample.

Nine human plasma samples from healthy subjects aged from 38 to 73 years, 9 human plasma samples from PD patients (38-85 years old) and 14 human plasma samples from patients with PDD (60-81 years old) were used for the α-synuclein assay using IMR. PD and PDD patients were identified using clinical symptoms. It is worth noting that PD patients are cognitively normal. All of the enrolled patients provided informed consent before undergoing the procedure and this invention was approved by National Taiwan University Hospital Research Ethics Committee.

The mean value of the hydrodynamic diameters for the antibody-functionalized magnetic $Fe_3O_4$ nanoparticles was found to be 55.5 nm and the standard deviation of particle hydrodynamic diameters was 12.7 nm. By using scanning electronic microscope, the mean value of the diameters for the antibody-functionalized magnetic $Fe_3O_4$ nanoparticles was obtained as ~40 nm. The reagent is superparamagnetic with the saturated magnetization of 0.3 emu/g. According to a previously published paper (*J Appl Phys* 2013, 144903-1-5), the numbers of antibody-functionalized nanoparticles in 1-ml reagent with 0.3 emu/g are around $10^{13}$. The total surface area of antibody-functionalized magnetic nanoparticles in 1-ml reagent is around 1000 $cm^2$. In experiment, 80-μl reagent is used. The total surface area of antibody-functionalized magnetic nanoparticles in 80-μl reagent for each assay is around 80 $cm^2$. As compared with a 96-well ELISA plate, the binding area between antibody and target bio-molecules for each well is 0.45 $cm^2$. Thus, the binding area with IMR is almost 180 times larger than that of ELISA.

Figure 1:
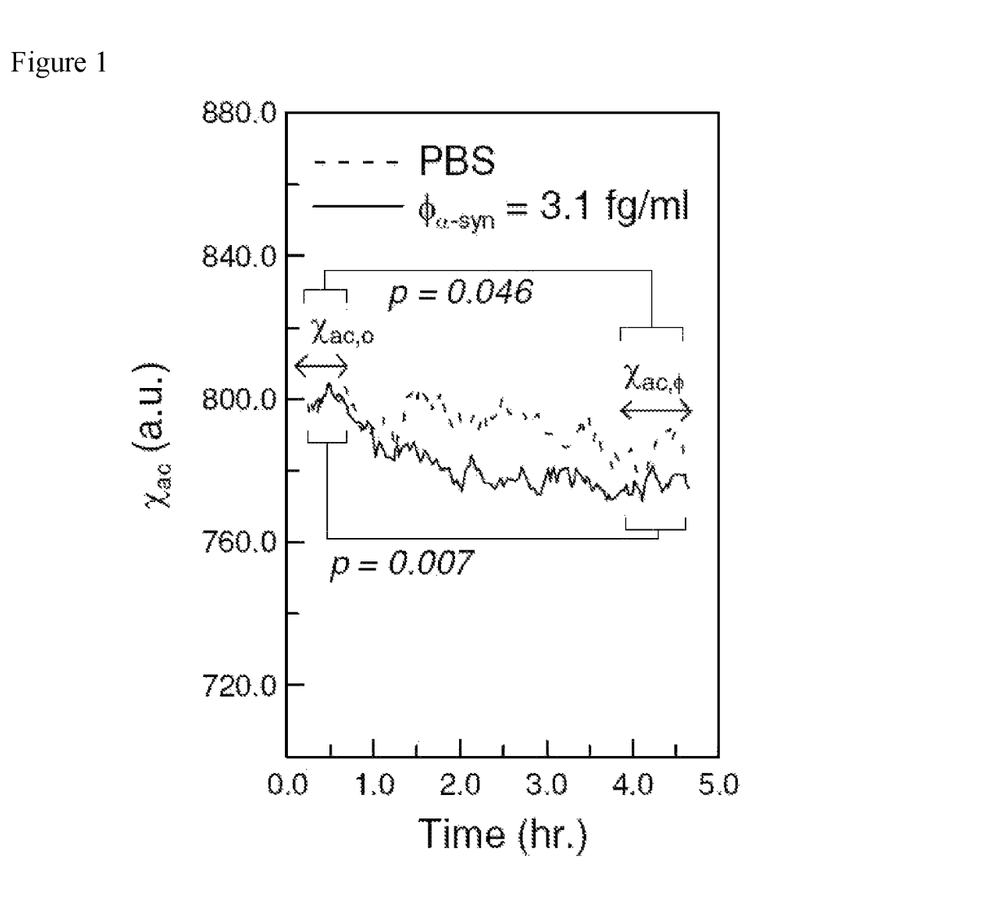
FIG. 1 illustrates the bio-activity test for the antibody immobilized on magnetic $Fe_3O_4$ nanoparticles using immunomagnetic reduction.

The bio-activity of the immobilized antibodies on magnetic nanoparticles is investigated by measuring the IMR signals. In one preferred embodiment, the machine comprises a magnetic sensor capable of detecting IMR signals. In a more preferred embodiment, the machine comprises a magnetic sensor for detecting the IMR signals by immobilizing antibodies against α-synuclein onto magnetic nanoparticles. In one yet more preferred embodiment, the magnetic sensor comprises a superconducting quantum interference device (SQUID) or a IMRhigh-$T_c$ SQUID magnetometer for detecting the IMR signals. The time dependent ac magnetic susceptibility $\chi_{ac}$ of reagent after mixing the reagent and the tested solution is recorded, as shown in FIG. 1. Two tested samples are prepared: one is pure PBS solution, the other is 3.1-fg/ml α-synuclein solution. The dashed line in FIG. 1 denotes the time dependent ac magnetic susceptibility $\chi_{ac}$ of the mixture of reagent and PBS solution. Clearly, temporal $\chi_{ac}$ with the dashed line almost remains unchanged. However, as to the solid line corresponding to the mixture of reagent and 3.1-fg/ml α-synuclein solution, the temporal $\chi_{ac}$ descends in 45 minutes and then reaches a lower level. A significant reduction in the ac magnetic susceptibility $\chi_{ac}$ of the reagent due to the association between α-synuclein and the antibodies on the magnetic nanoparticles is observed.

To quantify the reduction in the ac magnetic susceptibility $\chi_{ac}$ of the reagent, the initial/final $\chi_{ac}$ before/after the association between α-synuclein and antibodies on magnetic nanoparticles is calculated according to the temporal $\chi_{ac}$ shown in FIG. 1. As addressed in previously published papers (ACS Chem Neurosci. 2011; 2: 500-505; J Appl Phys 2010, 107: 074903-1-5), the confidence intervals for the determination of reduction in ac magnetic susceptibility $\chi_{ac}$ of the reagent are that within the first and the last 40-50 minutes of the time dependent ac magnetic susceptibility $\chi_{ac}$ shown in FIG. 1. In the present invention, the data of ac magnetic susceptibility $\chi_{ac}$ of the reagent within the first and the last 45 minutes are used for determining the reduction in) $\chi_{ac}$.

In FIG. 1, the p value for the ac magnetic susceptibility $\chi_{ac}$ between the intervals of the first and the last 45 minutes is found to be 0.046 for PBS solution. A slight reduction in the ac magnetic susceptibility $\chi_{ac}$ of reagent mixed with PBS is observed. As to 3.1-fg/ml α-synuclein solution, the p-value for the ac magnetic susceptibility $\chi_{ac}$ between the intervals of the first and the last 45 minutes is found to be 0.007. A clear reduction in the time dependent ac magnetic susceptibility $\chi_{ac}$ of reagent after being mixed with α-synuclein solution is evidenced.

The initial $\chi_{ac}$ is referred to as $\chi_{ac,o}$, which is the average value of $\chi_{ac}$'s within the first 45 minutes. The final $\chi_{ac}$ is referred to as $\chi_{ac,\varphi}$, which is the average value of $\chi_{ac}$'s within the last 45 minutes. The reduction in the ac magnetic susceptibility $\chi_{ac}$ of the reagent, e.g. IMR signal, is obtained via $$\text{IMR }(\%) = (\chi_{ac,o} - \chi_{ac,\varphi})/\chi_{ac,o} \times 100\% \qquad (1)$$

Via Eq.(1), the IMR signals for the dashed line and the solid line in FIG. 1 are calculated to be 1.56 and 2.13%, respectively. The results shown in FIG. 1 reveal a background level for the IMR assay. Such a background level is mainly attributed to the electronic noises of the assay system. According to the duplicate measurements, the IMR signals for the PBS solution are 1.56 and 1.65%. Thus, the background level of the IMR signal is 1.61% with a standard deviation of 0.06%.

Figure 2:
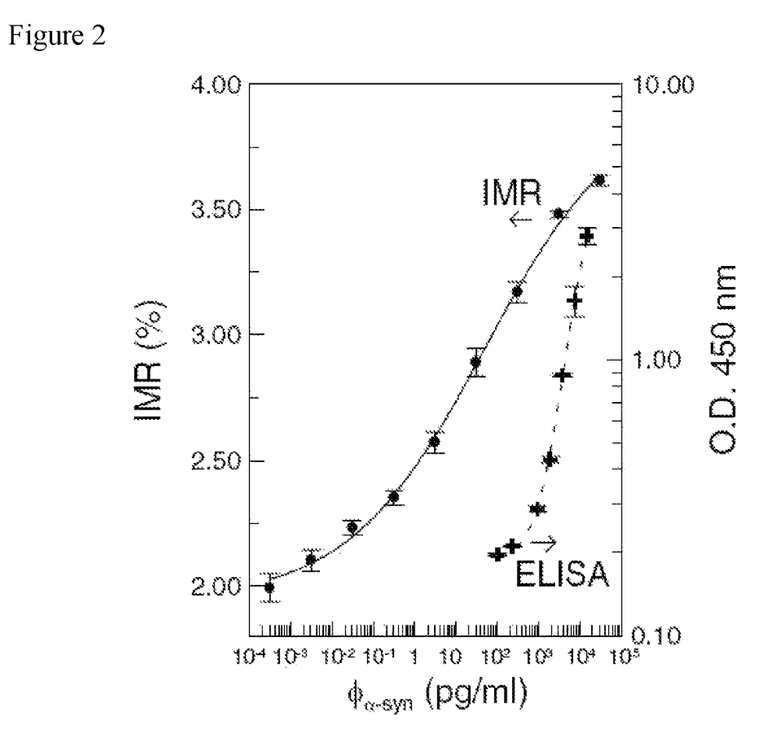
FIG. 2 illustrates α-synuclein concentration dependent IMR signal (solid line) and optical absorbance density at 450 nm, O.D. 450 nm (dashed line).

The IMR signal as a function of the concentration of α-synuclein, i.e. IMR (%)–$\varphi_{\alpha\text{-}syn}$ curve, is plotted in FIG. 2. As the concentration of α-synuclein $\varphi_{\alpha\text{-}syn}$ increases from $3 \times 10^{-4}$ pg/ml (=0.3 fg/ml), the IMR signal increases. The $\varphi_{\alpha\text{-}syn}$ dependent IMR (%) was found to follow the logistic function expressed as $$IMR(\%) = \frac{A-B}{1+\left(\frac{\varphi_{\alpha-syn}}{\varphi_o}\right)^\gamma} + B, \quad (2)$$

where A, B, $\varphi_o$ and $\gamma$ are fitting parameters. By fitting the data point in FIG. 2 to Eq. (2), the fitting parameters are obtained as A=1.94, B=3.95, $\varphi_o$=49.7 and $\gamma$=0.26. The fitting curve is plotted with the solid line in FIG. 2. The corresponding coefficient of determination $R^2$ is 0.998. The fact $R^2$ is very close to 1 implies $\varphi_{\alpha-syn}$ dependent IMR (%) is truly governed by the logistic function.

The parameter A in Eq.(2) is the value of IMR (%) as $\varphi_{\alpha-syn}$ extrapolates to zero. Usually, value A is a little higher than the background level. For example, A is 1.94% and the background level here is 1.61%. The difference between A and the background level is predominantly due to the noises caused by the dynamic equilibrium in the association between the protein molecules and the antibody-functional magnetic nanoparticles. However, A is not used as the low-detection limit Conventionally, the low-detection limit is defined as the concentration showing an IMR signal higher than A by three times as the standard deviation of IMR signals for a low-concentration test, i.e. 3-σ criterion. In this experiment, the standard deviation of low-concentration tests is 0.028%. Thus, the low-detection limit is the concentration having an IMR signal of 2.02%. Via Eq.(2), the low-detection limit for assaying α-synuclein is found to be 0.3 fg/ml.

The α-synuclein concentration dependent optical absorbance density at 450 nm, O.D. 450 nm, using ELISA is plotted by cross symbols in FIG. 2. The experimental data are fitted to the logistic function $$OD_{450} = \frac{A'-B'}{1+\left(\frac{\varphi_{\alpha-syn}}{\varphi_o'}\right)^{\gamma'}} + B' \quad (3)$$

The fitting parameters are found to be 0.189, 5.070, 13566.08 and 1.44 for A', B', $\varphi_o'$ and $\gamma'$ in Eq.(3). The logistic function of Eq.(3) is plotted by the dashed line in FIG. 2. The coefficient of determination $R^2$ between the cross symbols and the dashed line is 0.999. By utilizing the 3-σ criterion, the low-detection limit of assaying α-synuclein using ELISA is 79.04 pg/ml. It is obvious IMR is more sensitive than ELISA by a factor of 250,000 for assaying α-synuclein. As mentioned, the detecting sensitivity of IMR is higher than ELISA by a factor of 200 by taking the reacting surface into account. Additional factor of 1250 might be due to the ultra-low-noise magnetic sensor, i.e. high-$T_c$ superconducting quantum interference device (SQUID) magnetometer. High-$T_c$ SQUID magnetometer shows a noise level of 50 fT/Hz$^{1/2}$, which is lower than the magnetic signal generated by a single magnetic nanoparticle by three orders of magnitude. This implies that the reduction in ac magnetic signal resulted from a single magnetic nanoparticle due to the associating with target bio-molecule can be sensed by high-$T_c$ SQUID magnetometer. Hence, the ultra-low-noise high-$T_c$ SQUID magnetometer is extremely sensitive to the reduction in ac magnetic signal of reagent and shows ultra-high sensitivity in assaying bio-molecules.

Figure 3:
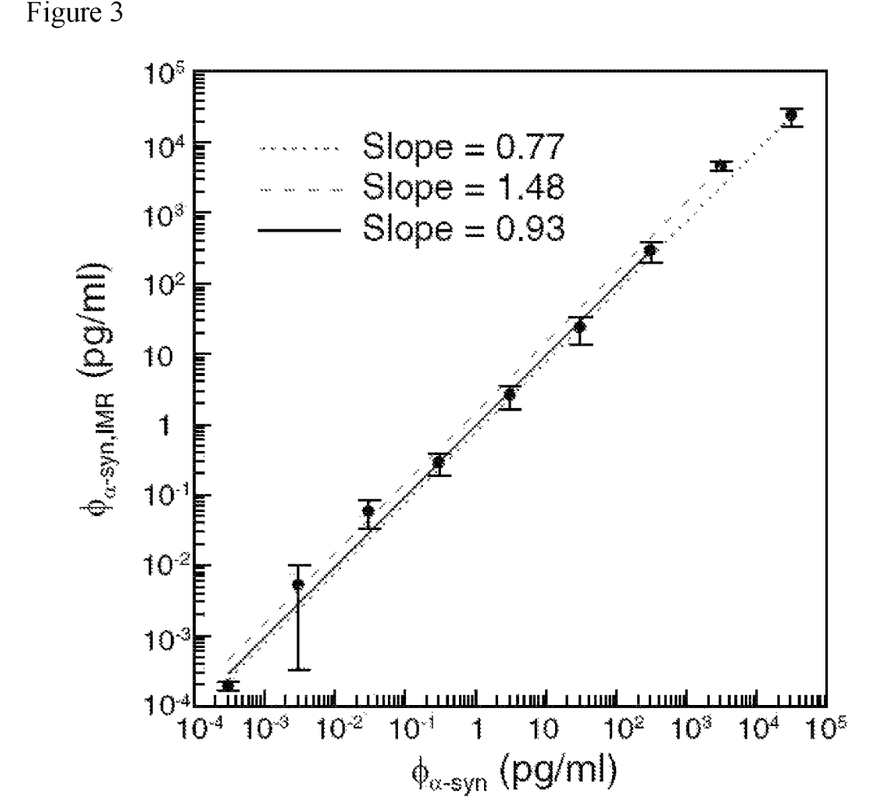
FIG. 3 illustrates Converted α-synuclein concentration $\varphi_{\alpha\text{-}syn,IMR}$ versus spiked α-synuclein concentration $\varphi_{\alpha\text{-}syn}$ in PBS solution for the analysis of dynamic range for assaying α-synuclein.

In addition to the low-detection limit, the dynamic range of assaying α-synuclein using IMR is an important characteristics. To examine the dynamic range, the experimental IMR signals in FIG. 2 are converted to concentrations of α-synuclein via Eq.(2). The converted concentrations of α-synuclein are denoted by $\varphi_{\alpha-syn,IMR}$. The correlation between $\varphi_{\alpha-syn,IMR}$ and $\varphi_{\alpha-syn}$ is examined, as shown in FIG. 3. In FIG. 3, the linearity between $\varphi_{\alpha-syn,IMR}$ and $\varphi_{\alpha-syn}$ can be obtained. According to the regulation issued by US Food and Drug Administration (FDA), the slope of the linearity in FIG. 3 must be between 0.90 and 1.10. In FIG. 3, if the $\varphi_{\alpha-syn,IMR}$'s for the α-synuclein concentration $\varphi_{\alpha-syn}$'s from 0.31 fg/ml to 31 ng/ml are used, the slope of the $\varphi_{\alpha-syn,IMR}$-$\varphi_{\alpha-syn}$ curve is 0.77 and the coefficient of determination $R^2$ is 0.991, as plotted by the dotted line in FIG. 3. The slope of the dotted line in FIG. 3 does not meet the requirement of the US FDA. The concentration range of α-synuclein for investigating the assay dynamic range should be narrowed. Hence, the highest $\varphi_{\alpha-syn,IMR}$ in FIG. 3, i.e. with $\varphi_{\alpha-syn}$ being 31 ng/ml, is ignored. The linear curve between $\varphi_{\alpha-syn,IMR}$ and $\varphi_{\alpha-syn}$ within the range from 0.31 to 3.1 ng/ml is plotted by the dashed line in FIG. 3. The slope of the dashed line is 1.48 and the coefficient of determination $R^2$ is 0.999. The slope of the dashed line is much higher than the requirement of the US FDA. It seems the second highest $\varphi_{\alpha-syn,IMR}$ in FIG. 3 should also be ignored. The linear curve between $\varphi_{\alpha-syn,IMR}$ and $\varphi_{\alpha-syn}$ within the range from 0.31 fg/ml to 310 pg/ml is plotted by the solid line in FIG. 3. The slope of the solid line is 0.93 and the coefficient of determination $R^2$ is 0.999. Notably, the slope of the solid line meets the requirement of the US FDA. Thus, the dynamic range of α-synuclein concentration for IMR assay is from 0.3 fg/ml to 310 pg/ml.

Figure 4:
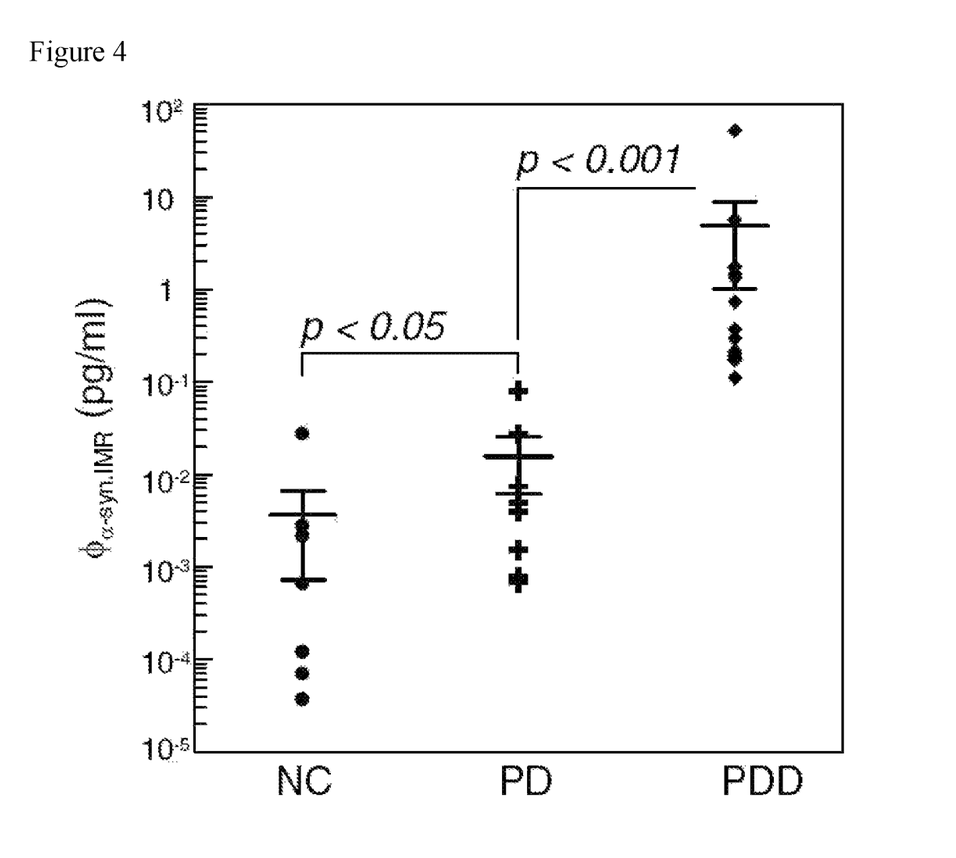
FIG. 4 illustrates Detected plasma α-synuclein concentrations using IMR for healthy subjects, PD patients and PDD patients.

The data shown in FIG. 2 prove the IMR assay is extremely sensitive and might possibly detect α-synuclein in human plasma. Plasma samples contributed by nine healthy persons, nine PD patients and fourteen PDD patients were collected for prior study on the discrimination between healthy subjects, PD patients and PDD patients by using IMR. The demographic information of the collected 33 subjects is listed in Table 1. The detected concentrations $\varphi_{\alpha-syn,IMR}$ of α-synuclein in human plasma are shown in FIG. 4. The plasma $\varphi_{\alpha-syn,IMR}$'s for PDD patients range from 0.1 to 100 pg/ml, while the plasma $\varphi_{\alpha-syn,IMR}$'s for healthy subjects are much lower than 0.1 pg/ml. The plasma $\varphi_{\alpha-syn,IMR}$'s for PD patients distribute between those of healthy subjects and PDD patients. The p value in terms of plasma $\varphi_{\alpha-syn,IMR}$ between healthy subjects and PD patients was found to be 0.005, which reveals the fact that PD patients show higher concentrations for plasma α-synuclein as compared to healthy subjects. In FIG. 4, a clear discrimination in plasma $\varphi_{\alpha-syn,IMR}$ between PD patients and PDD patients was observed (p<0.001). According to the results in FIG. 4, the concentration plasma α-synuclein keeps raising as a healthy subject suffering from PD and progressing to PDD. It is worth noting that the age is matched between healthy subjects and PD patients (p>0.05), as well as between PD patients and PDD patients (p>0.05).

TABLE 1

Demographic characteristics of the subjects

| Group | Healthy subjects | PD with normal cognition | PDD patients |
|---|---|---|---|
| Numbers | 9 | 9 | 14 |
| Female/Male | 4/5 | 4/5 | 7/7 |
| Age (years) | 38-73 | 38-85 | 60-81 |
| MMSE (mean ± SD) | 29.0 ± 1.1 | 28.7 ± 1.2 | 18.7 ± 6.3 |
| Disease duration (years) | — | 9.3 ± 6.7 | 10.1 ± 5.3 |

PD Parkinson disease;
PDD Parkinson disease dementia;
MMSE mini-mental state examination;
SD standard deviation Previous studies have shown that α-synuclein would be released from neurons by exocytosis into body fluids, including CSF and plasma, which contributes to cell-to-cell transmission of α-synuclein pathology in the brain. Numerous studies have focused on checking levels of either total or oligomeric α-synuclein in plasma samples from patients with PD compared with healthy controls but the results are conflicting. Since phosphorylated and fibrillar α-synuclein are the main pathological forms of the protein, one recent study observed that plasma level of phospho-α-synuclein was higher in early-stage PD samples without dementia than controls. These observations suggest the feasibility and potentiality of plasma level of α-synuclein (either total, oligomeric or phosphorylated form) could partly reflect the α-synuclein pathology in the brains of PD patients. Furthermore, cortical Lewy body/neuritic pathology is more extensive in PDD than in PD without dementia, which implies the α-synuclein burden in plasma is more severe in PDD than in PD. Our results supported this hypothesis that plasma level of α-synuclein is significantly higher in PDD than in PD with normal cognition, which level is slightly higher than healthy controls. As amyloid β plaques and tau neurofibrillary tangles, the hallmark pathologies of Alzheimer's dementia, are also observed and correlate with cognitive status in patients with PDD, future studies incorporating assessing phospho-α-synuclein, amyloid β protein, total and phospho-tau in plasma levels of PDD are needed to better understanding the pathophysiology of PDD.

In plasma samples, heterophilic antibody is a major confounder and interferes the assaying results by sandwich ELISA method. Heterophilic antibody (HA) is defined as one of the common interference materials for immunoassay according to the guidance of Clinical and Laboratory Standards Institute (CLSI-EP-A2: Interference Testing of Clinical Chemistry). IMR method showed low-interference and high-specificity effects in comparison with ELISA through previous researches. The selection mechanism is based on centrifugation force contributed from oscillating magnetic nanoparticles in reagent. The details have been discussed in previous research. In fact, not only HA but also naturally existed biomolecules of frequently used drug in plasma are prevented from associating with magnetic nanoparticles via the selection mechanism. This features IMR a high-specificity methodology for clinical analysis of plasma biomarkers of Parkinson's disease.

Clinically, patients first are diagnosed with PD and in later stages of the disease may develop dementia and thus get the diagnosis of PDD; Hence, biomarkers that can predict or diagnose early stages of progression to PDD in PD subject would indeed be of clinical significance. According to the results in FIG. 4, the plasma α-synuclein in PDD patients show clearly higher level than that in PD patients (p<0.001). This implies that plasma α-synuclein is promisingly used as a clinical parameter monitoring the progression to PDD in PD patients.

Figure 5:
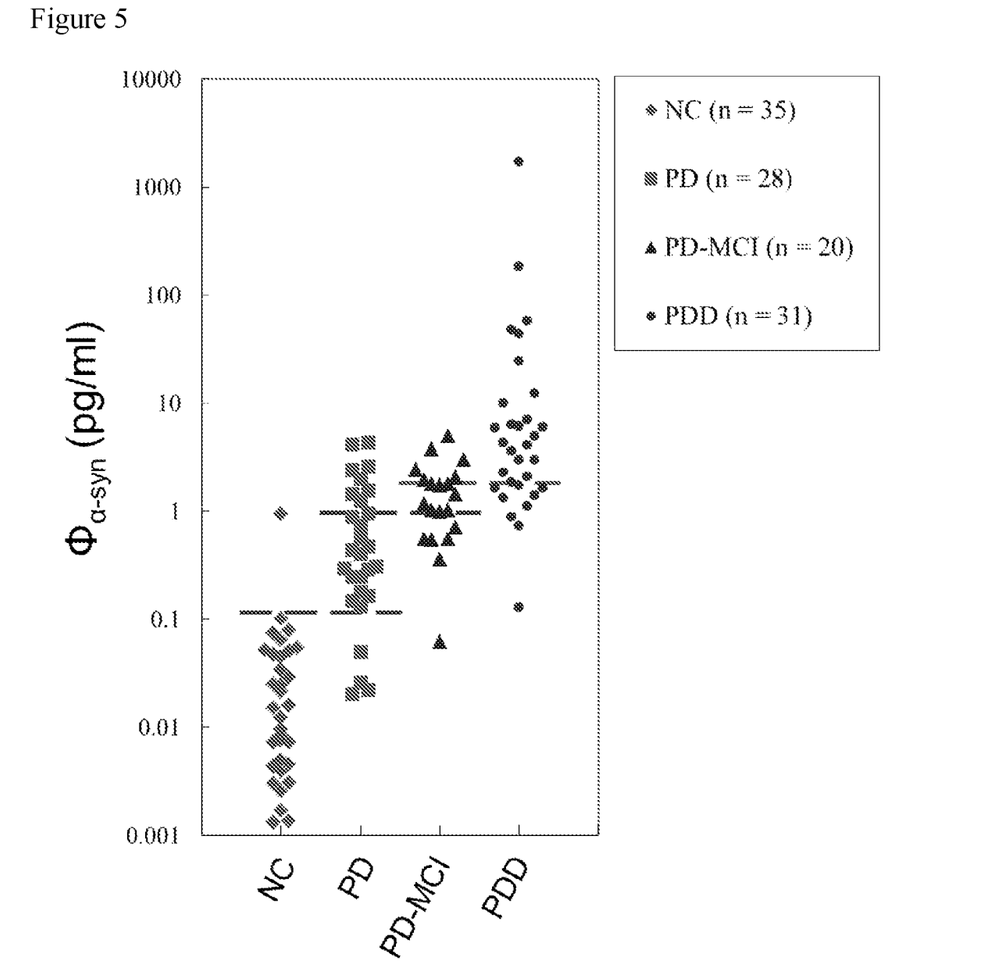
FIG. 5 illustrates Plasma $\varphi\alpha\text{-}syn, IMR$s in PD patients with varying cognitive function.

In a further embodiment, the detected concentrations $\varphi_{\alpha\text{-}syn}$,IMR of α-synuclein in human plasma from 114 subjects (35 of normal control group and 79 of PD patients) are shown in FIG. 5. The median plasma $\varphi\alpha\text{-}syn$,IMRs was 0.1161 pg/mL for PD with normal cognition, 0.965 pg/mL for PD with mild cognitive impairment (PD-MCI) and 1.814 pg/mL for PDD, respectively (p<0.0001 by Kruskal-Wallis test).

By immobilizing antibodies against α-synuclein onto magnetic nanoparticles, the reagent for assaying α-synuclein is developed. Through utilizing immunomagnetic reduction (IMR) with aid of high-$T_c$ SQUID magnetometer, the dynamic range of assaying α-synuclein is from 0.3 fg/ml to 310 pg/ml. The ultra-sensitivity SQUID-based IMR is applied to assay human plasma α-synuclein. The preliminary results show a clear difference in the concentrations of plasma α-synuclein between healthy subjects, PD patients and PDD patients. This method seems promising to apply IMR to diagnosis of PD and PDD by assaying plasma α-synuclein.

What is claimed is:

1. A method for clinically identifying Parkinson's disease with normal cognition or Parkinson's disease dementia in a subject, comprising:
   (a) detecting in vitro immunomagnetic reduction (IMR) signals of α-synuclein in a blood sample of the subject, wherein the IMR signals are produced by binding α-synuclein with magnetic nanoparticles containing antibody against α-synuclein;
   (b) fitting the IMR signals of α-synuclein detected in step (a) to a logistic function (I) to calculate α-synuclein's concentration in the blood sample:

$$IMR(\%) = \frac{A - B}{1 + \left(\frac{\varphi_{\alpha\text{-}syn}}{\varphi_o}\right)^\gamma} + B, \quad (I)$$

wherein IMR (%) is the IMR signals of α-synuclein, $\varphi_{\alpha\text{-}syn}$ is the concentration of α-synuclein, fitting parameter A is a background value, B is a maximum value, $\varphi_o$ is the concentration of α-synuclein when IMR signal equals ((A+B)/2), γ is a slope at data point $\varphi_o$ of a curve where $\varphi_{\alpha\text{-}syn}$ is x-axis and IMR (%) is y-axis; and
   (c) comparing the concentration obtained in step (b) to a predetermined range, wherein a concentration higher than the predetermined range is indicative of Parkinson's disease dementia in the subject, a concentration inside of the predetermined range is indicative of Parkinson's disease with normal cognition in the subject, and a concentration lower than the predetermined range is indicative of a healthy subject.

2. The method of claim 1, wherein the magnetic nanoparticles comprise a material selected from the group consisting of $Fe_3O_4$, $Fe_2O_4$, $MnFe_2O_4$, $CoFe_2O_4$ and $NiFe_2O_4$.

3. The method of claim 1, wherein the magnetic nanoparticles comprise $Fe_3O_4$.

4. The method of claim 1, wherein the blood sample is plasma.

5. The method of claim 1, wherein the IMR signals of α-synuclein in the blood sample are detected with a machine capable of detecting IMR signals.

* * * * *